United States Patent [19]

De Vincentiis

[11] 4,317,917

[45] Mar. 2, 1982

[54] DERIVATIVES OF METHYL-SUBSTITUTED OR METHOXY-SUBSTITUTED 2-HYDROXYBENZOIC ACIDS, AND PHARMACEUTICAL FORMULATIONS CONTAINING THEM

[75] Inventor: Leonardo De Vincentiis, Pomezia, Italy

[73] Assignee: Ausonia Farmaceutici S.r.l., Rome, Italy

[21] Appl. No.: 132,517

[22] Filed: Mar. 21, 1980

[30] Foreign Application Priority Data

May 17, 1979 [IT] Italy ............................. 22739 A/79

[51] Int. Cl.³ ............................................. C07C 69/88
[52] U.S. Cl. ...................................... 560/72; 560/71; 560/64; 560/66; 560/104; 424/308
[58] Field of Search ........................ 560/71, 72, 64, 66, 560/104

[56] References Cited

U.S. PATENT DOCUMENTS 2,246,974  6/1941  Coleman et al. ................... 560/104
3,396,193  8/1968  Freedman et al. ................. 560/104

OTHER PUBLICATIONS

Kramer, P. A. et al., J.A.C.S. |91:10| May 7, 1969, pp. 2600-2608.
Ramakrishnan, V. T. et al. J. Org. Chem., vol. 35, No. 9, 1970, pp. 2901-2904.

Primary Examiner—Paul J. Killos
Attorney, Agent, or Firm—Bucknam and Archer

[57] ABSTRACT

The invention relates to methyl- or methoxy-substituted 2-cynnamoyloxy-benzoic acids or to cynnamylesters of methyl- or methoxy-substituted 2-hydroxybenzoic acids, endowed with an interesting antiinflammatory, analgesic and antibacterial activity; and to a process for preparing said compounds.

9 Claims, No Drawings

DERIVATIVES OF METHYL-SUBSTITUTED OR METHOXY-SUBSTITUTED 2-HYDROXYBENZOIC ACIDS, AND PHARMACEUTICAL FORMULATIONS CONTAINING THEM

This invention relates to derivatives of methyl-substituted or methoxy-substituted 2-hydroxybenzoic acids of general formula (I)

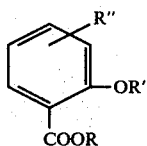

in which:

R represents hydrogen, and R' represents the cinnamoyl residue (3-phenyl-2-propenoyl); or R represents cinnamyl (3-phenyl-2-propenyl), and R' represents hydrogen; and R" represents CH₃ or OCH₃.

The compounds (I) have marked antiinflammatory, analgesic and antibacterial activity, accompanied by very low toxicity, an excellent local tolerability, and an ulcerogenic action which is certainly less than that of known drugs. Consequently, the invention also relates to pharmaceutical formulations of antiinflammatory, analgesic and antibacterial activity containing one or more compounds of formula (I) as their active principle. Finally, the invention also relates to a process for preparing compounds of formula (I), characterised in that (a) methyl- or methoxy-2-hydroxybenzoic acids are reacted with cinnamyl alcohol (3-phenyl-2-propen-1-ol) in the presence of acid catalysts, or (b) an activated derivative of cinnamic acid (3-phenyl-2-propenoic acid) is reacted with a methyl- or methoxy-2-hydroxy-benzoic acid, in accordance with the scheme:

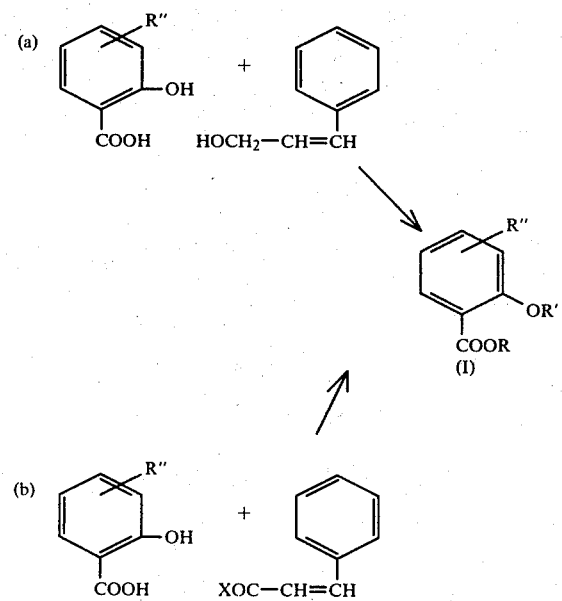

in which R, R' and R" have the aforesaid meanings, and X represents a halogen atom, and alkoxyl residue or a residue such as to form a mixed anhydride with the 3-phenyl-2-propenoyl group. Preferably, reaction (a) is catalysed by anhydrous phosphoric acid, whereas in reaction (b) 3-phenyl-2-propenoyl chloride is used.

The examples given hereinafter illustrate the process according to the invention, but without limiting it. The structure of the described compounds has been confirmed by analytical and spectroscopic data.

EXAMPLE 1

(3-Phenyl-2-hydroxy-5-methylbenzoate 40.251 g of 3-phenyl-2-propen-1-ol (0.3 moles) and 4.9 g of anhydrous phosphoric acid (0.05 moles) are added to 15.24 g of 2-hydroxy-5-methylbenzoic acid (0.1 moles). The mixture is heated to 95°–100° C. under stirring for 24 hours. It is then cooled, and dissolved in 200 ml of ether.

The ether solution is extracted with water until the phosphoric acid is removed, then with 50 ml of a 10% potassium carbonate solution. The aqueous alkaline solution is acidified with 2N HCl. The solid precipitate is removed by filtration and washed with water heated to 60°–70° C.

The crude product is crystallised from 60% methanol. 24 g (yield 89.4%) of (3-phenyl-2-propenyl)-2-hydroxy-5-methylbenzoate are obtained, having a m.p. of 178.5°–179° C.

EXAMPLE 2

(3-Phenyl-2-propenyl)-2-hydroxy-4-methylbenzoate

Using the method of example 1, 15.24 g of 2-hydroxy-4-methylbenzoic acid (0.1 moles), 40.251 g of 3-phenyl-2-propen-1-ol (0.3 moles) and 4.9 g of anhydrous phosphoric acid (0.05 moles) give 23.9 g (89% yield) of (3-phenyl-2-propenyl)-2-hydroxy-4-methylbenzoate, m.p. 196°14 196.5° C.

EXAMPLE 3

(3-Phenyl-2-propenyl)-2-hydroxy-3-methylbenzoate

Using the method of example 1, 15.24 g of 2-hydroxy-3-methylbenzoic acid (0.1 moles), 40.251 g of 3-phenyl-2-propen-1-ol (0.3 moles) of 4.9 g of anhydrous phosphoric acid (0.05 moles) give 23.9 g (yield 89%) of (3-phenyl-2-propenyl)-2-hydroxy-3-methylbenzoate, m.p. 154°–154.5° C.

EXAMPLE 4

2-(3-Phenyl-2-propenoyloxy)-5-methylbenzoic acid 20.82 g. of SOCl₂ (0.175 moles) are added to 14.815 g(0.1 moles) of 3-phenyl-2-propenoic acid, and the mixture heated under reflux for 8 hours. The excess SOCl₂ is then distilled off under reduced pressure. The residue is taken up in 250 ml of anhydrous benzene, and a suspension of 15.24 g of 2-hydroxy-5-methylbenzoic acid (0.1 moles) in 250 ml of anhydrous benzene is added.

The mixture is heated under reflux for about 35 hours, is then cooled and extracted with a 5% aqueous potassium carbonate solution. The separated alkaline solution is acidified with 2N HCl. The solid precipitate is removed by filtration and washed with water heated to 60°–70° C.

The crude product is first crystallised from glacial acetic acid, then from 60% methanol.

23 g of 2-(3-phenyl-2-propenoyloxy)-5-methylbenzoic acid (yield 81.47%) are obtained, having a m.p. of 161.5°–162° C.

EXAMPLE 5

2-(3-Phenyl-2-propenoyloxy)-4-methylbenzoic acid

Using the method of example 4, 14.815 g (0.1 moles) of 3-phenyl-2-propenoic acid and 20.82 g of $SOCl_2$ (0.175 moles) followed by 15.24 g of 2-hydroxy-4-methylbenzoic acid (0.1 moles) give 22.4 g of 2-(3-phenyl-2-propenoyloxy)-4-methylbenzoic acid (yield 81.1%), m.p. 156.5°–157° C.

EXAMPLE 6

2-(3-Phenyl-2-propenoyloxy)-3-methylbenzoic acid

Using the method of example 4, 14.815 g(0.1 moles) of 3-phenyl-2-propenoic acid and 20.82 g of $SOCl_2$ (0.175 moles) followed by 15.24 g of 2-hydroxy-3-methylbenzoic acid (0.1 moles) give 23.1 g of 2-(3-phenyl-2-propenoyloxy)-3-methylbenzoic acid (yield 81.8%), m.p. 141°–141.5° C.

EXAMPLE 7

(2-propenyl-3-phenyl)-2-hydroxy-3-methoxy-benzoate

Using the method of example 1, 16.814 g (0.1 moles) of 2-hydroxy-3-methoxybenzoic acid, 40.251 g of 3-phenyl-2-propen-1-ol (0.3 moles) and 4.9 g of anhydrous phosphoric acid (0.05 moles) give 26.838 g (yield 90%) of (2-propenyl-3-phenyl)-2-hydroxy-3-methoxy-benzoate.

The characteristics of high activity and practical absence of side effects of the products according to the invention are illustrated hereinafter by way of example, for 2-(3-phenyl-2-propenoyloxy)-5-methylbenzoic acid (see example 4), indicated by the symbol AF1 for brevity.

1. Acute toxicity

Acute toxicity of the product was studied in the Swiss mouse and Wistar rat by oral and intraperitoneal administration. The substance was carried in 5% gum arabic for both methods of administration. The volumes inoculated for both methods of administration were 20 ml/kg of body weight for the mouse and 5 ml/kg for the rat. The $LD_{50}$ values expressed in mg/kg were calculated on the seventh day of treatment by the probital analysis method.

The results are given in table 1.

TABLE 1

| | $LD_{50}$ values in mg/kg and their 95% reliability limits (given in brackets) | |
|---|---|---|
| Animal | Administration method | AF1 |
| Mouse | oral | 901.8 (877.4–926.8) |
|  | i.p. | 410.1 (373.9–451.1) |
| Rat | oral | >2000 |
|  | i.p. | 733.8 (696.0–775.0) |

2. Subacute toxicity in the rat by intramuscular administration

The test was carried out for 25 consecutive days using drug doses of 60 and 120 mg/kg/die. The condition of the rats was always excellent, neither were there significant changes in general condition and weight.

3. Local tolerability check

A 0.5 solution of AF1 dropped into the conjunctival sac of the eye of a rabbit caused no irritating or otherwise damaging modification to local tissues. In addition, intramuscular administration of the product at a dose of 60–120 mg/kg/die for 25 consecutive days, carried out on the rat by subchronic treatment, led to no macroscopic change in the tissues where the drug was introduced, neither were other undesirable local phenomena observed.

4. Antiinflammatory activity

4.1 Edema by carrageen

The antiinflammatory activity of AF1 was evaluated in comparison with that of a known drug (Tanderil ®) by inhibiting the edema induced in the rear paw of the rat by carrageen. The method used is that described by Winter.

The substances examined were administered orally to Wistar rats having a body weight of 165±15 g.

The percentage edema inhibition for the various groups of animals was calculated by putting the average percentage increase of the control group equal to 100.

The results are shown in table 2.

TABLE 2

| | Edema by carrageen | | |
|---|---|---|---|
| | | Percentage edema inhibition relative to the controls at the following times after edematigenous treatment (average values) | |
| No. animals | Treatment mg/kg by oral administration | 4 hours | 6 hours |
| 15 | Tanderil 25 | 58 | 68 |
| 15 | Tanderil 50 | 56 | 78 |
| 15 | AF1 25 | 42 | 71 |
| 15 | AF1 50 | 62 | 84 |
| 15 | AF1 75 | 73 | 87 |

4.2 Edema by kaolin

The antiedematous action of AF1 was also investigated by the test of Conbon and coll. (Arch.Int.Pharmacodyn. 99; 474, 1954), consisting of measuring the diameter of the tibiotarsal joint in both the rear paws of the rat. Groups of five animals representing controls and treated animals were used for two separate experiments. 0.2 ml of a sterile 10% kaolin suspension was injected directly into the joint of the two rear paws of each animal.

The joint diameter was measured one hour after the kaolin injection and then every 24 hours afterwards for five consecutive days. The AF1 compound was administered intraperitoneally in a quantity of 100 mg/kg one hour after the kaolin injection and at the same time on the following days over the entire test period.

The results are shown in table 3.

TABLE 3

| Edema by kaolin. Effect of AF1 on edema induced by kaolin. | | | |
|---|---|---|---|
| | | Average of diameters (mm) Mean values | |
| Time after treatment with kaolin. Days | Controls | Treated animals | % inhibition relative to controls |
| 0 | 5.9 | 5.8 | — |
| 0 + 1 hour | 6.6 | 6.9 | — |
| 1 | 9.9 | 8.8 | −11.1 |
| 2 | 10.2 | 8.7 | −14.7 |
| 3 | 10.9 | 8.0 | −26.6 |
| 4 | 10.3 | 7.9 | −23.3 |
| 5 | 10.1 | 7.5 | −25.7 |

5. Analgesic activity

The analgesic activity of the compound under examination was tested in the mouse by the method of Ben Bassat and coll. (Arch. Int. Pharmacodyn, 122, 434, 1954) and comparing the drug in question with Tanderil ® (T).

The relative results are illustrated in table 4.

TABLE 4

Analgesic action of the new drug and Tanderil ® in the mouse.

| No. ani-mals | Treatment mg/kg by oral admi-nistration | | % Increase in the painful reaction time relative to the controls, at the following minutes after administration | | | | |
|---|---|---|---|---|---|---|---|
| | | | 30 min. | 60 min. | 90 min. | 120 min. | 150 min. |
| 20 | T | 100 | 11 | 14 | 15 | 20 | 21 |
| 20 | AF1 | 100 | 22 | 32 | 36 | 48 | 51 |

6. Ulcerogenic action

The ulcerogenic action of the product was evaluated in the female Wistar rat in comparison with that of other known antiinflammatory drugs.

Animals were used having a body weight of between 150 and 180 g, and which had fasted for 24 hours before treatment. The products were administered orally in a dose corresponding to about two fifths their $LD_{50}$.

The animals were sacrificed four hours after treatment, and the stomachs examined to check any presence of ulcers.

The results are given in table 5.

TABLE 5

Ulcerogenic action

| Product | Dose mg/kg | No. of ulcerated animals/ No. of treated animals |
|---|---|---|
| AF1 | 400 | 0/10 |
| AF1 | 800 | 1/10 |
| Naproxen | 200 | 5/10 |
| Phenylbutazone | 200 | 4/10 |

Even in mice treated for 5 consecutive days with 200 mg/kg per day of AF1, there was no sign of any gastric or duodenal lesion.

7. "In vitro" antibacterial activity

The antiseptic power of the substance under examination was evaluated by determining the minimum inhibiting concentration (C.M.I.) on a series of Gram negative and Gram positive germs related to the pathology of the respiratory tree.

The culture broth used was Difco nutrient broth, and 8 test samples were used for each concentration tested. Guaiacol was used as the comparison drug.

The results are given in table 6.

TABLE 6

Minimum inhibiting concentration on the following microorganisms - (mcg/ml)

| (Gram) | Haemophilus influeniae (−) | Sarcina lutea (+) | Micrococ-cus catar-rhalis (−) | Micro-coccus pyoge-nes (+) | Micrococ-cus tuberc. (bovis) (+) |
|---|---|---|---|---|---|
| Product | | | | | |
| Guaiacol | 33,000 | 33,000 | 16,600 | 33,000 | 33,000 |
| AF1 | 16,000 | 9,150 | 4,300 | 16,600 | 3,150 |

The compounds of the invention can be used in therapy in various pharmaceutical formulations, examples of which are as follows, in each case with reference to 2-(3-phenyl-2-propenoyloxy)-5-methylbenzoic acid (AF1).

| 100 mg tablets | |
|---|---|
| AF1 | 100 mg |
| lactose | 150 mg |
| potato starch | 30 mg |
| magnesium stearate | 2 mg |
| | 282 mg |
| 100 mg pills | |
| AF1 | 100 mg |
| lactose | 100 mg |
| corn starch | 30 mg |
| magnesium stearate | 2 mg |
| | 232 mg |
| 200 mg capsules | |
| AF1 | 200 mg |
| lactose | 150 mg |
| corn starch | 30 mg |
| magnesium stearate | 2 mg |
| | 382 mg |
| 150 mg suppositories | |
| AF1 | 150 mg |
| base for suppositories (semisynthetic glycerides) | 1550 mg |
| | 1700 mg |
| 300 mg vaginal ovules | |
| AF1 | 300 mg |
| base for ovules (semisynthetic glycerides) quantity required to total | 2400 mg 2700 mg |
| 3% dermatological ointment | |
| AF1 | 3 g |
| ethyl alcohol | 70 g |
| vaseline oil | 100 g |
| 50 cm³ spray | |
| Each 50 cm³ bottle contains: | |
| micronised AF1 | 1.000 g |
| calcium stearate | 0.500 g |
| isopropyl myristate | 40.000 g |
| compressed nitrogen quantity required to total | 50 cm³ |

I claim:

1. Derivatives of methyl-substituted or methoxy-substituted 2-hydroxybenzoic acids of general formula (I)

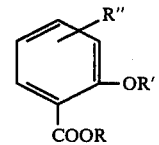

in which:

R represents hydrogen, and R' represents the cinnamoyl residue (3-phenyl-2-propenoyl); or R represents cinnamyl (3-phenyl-2-propenyl), and R' represents hydrogen; and R" represents $CH_3$ or $OCH_3$.

2. A compound as claimed in claim 1, which is (2-propenyl-3-phenyl)-2-hydroxy-5-methyl benzoate.

3. A new compound as claimed in claim 1, which is (2-propenyl-3-phenyl)-2-hydroxy-4-methyl-benzoate.

4. A new compound as claimed in claim 1, which is (2-propenyl-3-phenyl)-2-hydroxy-3-methyl-benzoate.

5. A new compound as claimed in claim 1, which is 2-(3-phenyl-2-propenoyloxy)-5-methylbenzoic acid.

6. A new compound as claimed in claim 1, which is 2-(3-phenyl-2-propenoyloxy)-4-methylbenzoic acid.

7. A new compound as claimed in claim 1, which is 2-(3-phenyl-2-propenoyloxy)-3-methylbenzoic acid.

8. A new compound as claimed in claim 1, which is (2-propenyl-3-phenyl)-2-hydroxy-3-methoxybenzoate.

9. Pharmaceutical compositions of antiinflammatory, analgesic and antibacterial activity, characterised by containing at least one compound as claimed in claim 1 as their active principle.

* * * * *